(12) United States Patent
Kwon et al.

(10) Patent No.: US 12,245,688 B2
(45) Date of Patent: Mar. 11, 2025

(54) ARM REST APPARATUS

(71) Applicants: ROEN Surgical, Inc., Daejeon (KR); KOREA ADVANCED INSTITUTE OF SCIENCE AND TECHNOLOGY, Daejeon (KR)

(72) Inventors: Dong Soo Kwon, Daejeon (KR); Duk Sang Kim, Daejeon (KR); Byung Sik Cheon, Daejeon (KR); Un Je Yang, Daejeon (KR)

(73) Assignees: ROEN Surgical, Inc., Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 462 days.

(21) Appl. No.: 17/503,858

(22) Filed: Oct. 18, 2021

(65) Prior Publication Data

US 2022/0031065 A1 Feb. 3, 2022

Related U.S. Application Data

(63) Continuation-in-part of application No. PCT/KR2020/004534, filed on Apr. 2, 2020.

(30) Foreign Application Priority Data

Apr. 23, 2019 (KR) .......................... 10-2019-0047445

(51) Int. Cl.
*A47B 21/03* (2006.01)
*A47C 7/54* (2006.01)
(Continued)

(52) U.S. Cl.
CPC .......... *A47B 21/0371* (2013.01); *A47C 7/541* (2018.08); *A47C 7/546* (2013.01);
(Continued)

(58) Field of Classification Search
CPC ........ A47B 21/0371; A47B 2021/0392; A47C 7/541; A47C 7/546; A47C 20/023;
(Continued)

(56) References Cited

U.S. PATENT DOCUMENTS 1,266,367 A * 5/1918 Wison ..................... A01K 87/08
43/25
1,516,795 A * 11/1924 Schwarting ............ A61G 13/12
43/25
(Continued)

FOREIGN PATENT DOCUMENTS

CN 103707320 4/2014
CN 203790256 U 8/2014
(Continued)

*Primary Examiner* — Kimberly T Wood
(74) *Attorney, Agent, or Firm* — JCIPRNET

(57) ABSTRACT

An arm rest apparatus, according to one embodiment, may comprise: a fixed part fixed to an external object; a horizontal movement module having one end rotatably connected to the fixed part and the other end having two-translational-degree-of-freedom movement with respect to the fixed part; and an arm support module installed to have two rotational degrees of freedom with respect to the other end of the horizontal movement module.

8 Claims, 8 Drawing Sheets

(51) Int. Cl.
*A47C 20/02* (2006.01)
*B25J 17/02* (2006.01)

(52) U.S. Cl.
CPC ......... *A47C 20/023* (2013.01); *B25J 17/0266* (2013.01); *A47B 2021/0392* (2013.01)

(58) Field of Classification Search
CPC ..... A47C 16/00; B25J 17/0266; B25J 9/0006; B25J 9/1065; B25J 13/02; B25J 9/109; B25J 9/16; A61B 90/60
See application file for complete search history.

(56) References Cited

U.S. PATENT DOCUMENTS

| | | | | |
|---|---|---|---|---|
| 2,119,325 | A * | 5/1938 | Goodhart | A61M 5/52 248/118 |
| 2,614,558 | A * | 10/1952 | Lovell | A61F 5/04 248/118 |
| 3,124,328 | A * | 3/1964 | Kortsch | A61G 15/12 248/278.1 |
| 4,592,526 | A * | 6/1986 | Kobelt | F16C 11/10 248/284.1 |
| 4,648,785 | A | 3/1987 | Nakagawa et al. | |
| 5,571,274 | A * | 11/1996 | Holstensson | A47C 1/03 297/411.36 |
| 5,655,814 | A * | 8/1997 | Gibbs | A47C 1/03 248/118 |
| 5,884,974 | A * | 3/1999 | Bergsten | A47B 21/0371 297/411.36 |
| 6,042,064 | A * | 3/2000 | Hong | A47B 21/0371 248/278.1 |
| 6,663,055 | B2 * | 12/2003 | Boucher | A61G 13/0045 248/118 |
| 6,786,461 | B1 * | 9/2004 | Tsai | B43M 99/00 248/292.12 |
| 6,925,668 | B2 * | 8/2005 | Cuschieri | A61B 90/60 5/621 |
| 7,222,826 | B1 * | 5/2007 | Berglund | A47B 21/0314 248/118 |
| 7,823,843 | B2 * | 11/2010 | Oberlaender | F16M 11/2092 248/278.1 |
| 9,204,730 | B2 * | 12/2015 | Brown | A47C 7/52 |
| 10,792,183 | B2 * | 10/2020 | Hoffman | A61F 5/3769 |
| 2003/0028967 | A1 * | 2/2003 | Schuerch | A61G 13/12 5/621 |
| 2005/0075739 | A1 * | 4/2005 | Nishizawa | B25J 9/1065 700/56 |
| 2010/0193457 | A1 | 8/2010 | Rotheisler | |
| 2017/0173783 | A1 * | 6/2017 | Angold | B25J 9/109 |
| 2018/0361565 | A1 * | 12/2018 | Angold | B25J 9/106 |

FOREIGN PATENT DOCUMENTS

| | | |
|---|---|---|
| CN | 105983850 | 10/2016 |
| EP | 1669038 | 6/2006 |
| EP | 2907467 | 8/2015 |
| KR | 20-0280389 Y1 | 7/2002 |
| KR | 200280389 | 7/2002 |
| KR | 10-2014-0103655 A | 8/2014 |
| KR | 20140103655 X | 8/2014 |
| KR | 101603162 | 3/2016 |
| KR | 10-1731910 B1 | 5/2017 |
| KR | 10-1903904 B1 | 11/2018 |
| KR | 20190003280 | 1/2019 |
| WO | 2018052226 | 3/2018 |

* cited by examiner

ARM REST APPARATUS

CROSS-REFERENCE TO RELATED APPLICATIONS

This application is a continuation-in-part of PCT/KR2020/004534 filed Apr. 2, 2020, which claims priority to KR 10-2019-0047445, filed Apr. 23, 2019, the entire disclosure of which is incorporated herein by reference.

BACKGROUND OF THE INVENTION

1) Technical Field

The present invention relates to an arm rest apparatus.

2) Description of Related Art

An arm rest supports parts of the arm and the hand of a user so as to improve the precision in movement of the arm, to improve arm shaking, and to reduce the degree of fatigue in movement of the arm.

However, most of conventional arm rest structures are to simply support a part of the arm, and are difficult to support the arm stably and uniformly in various arm poses when an arm position and an arm angle is changed in a working space.

Therefore, there is a growing need for an arm rest apparatus, which can guide movement of the arm accurately through an ergonomic movement according to changes in the user's arm movements or arm poses and can effectively relieve the user's manipulation fatigue.

The conventional background art was acquired or held while the inventor of the present invention derived the present invention, and so, it is not necessarily the prior art opened to the public before application of the present invention.

Accordingly, the present invention has been made in an effort to solve the above-mentioned problems occurring in the prior arts, and it is an object of the present invention to provide an arm rest apparatus.

BRIEF SUMMARY OF THE INVENTION

To achieve the above objects, the present invention provides an arm rest apparatus including: a fixed part fixed to an external object; a horizontal movement module having one end rotatably connected to the fixed part and the other end having two-translational-degree-of-freedom movement with respect to the fixed part; and an arm support module movably supported by the horizontal movement module.

The horizontal movement module includes: a first driving frame which has a first link rotatably connected to a first rotary shaft and rotatably connected to a second rotary shaft parallel with the first rotary shaft; a second driving frame which has a driving link rotatably connected to the first rotary shaft, a second link rotatably connected to a third rotary shaft parallel with the first rotary shaft, and a third link rotatably connected to a fourth rotary shaft spaced apart from the third rotary shaft in parallel with the third rotary shaft and rotatably connected to the second rotary shaft; a central connection part which is rotatably connected to the fixed part through a plurality of links; and a rotational end part which is rotatably connected to the central connection part through a plurality of links.

The horizontal movement module further includes a fourth link which is rotatably connected to the second rotary shaft and is rotatably connected to a fifth rotary shaft parallel with the first rotary shaft, and the fourth link is fixed to the third link so as to rotate around the second rotary shaft together.

The first driving frame further comprises a first protrusion member which is fixed to the first link to rotate around the first rotary shaft and has an edge radially protruding around the first rotary shaft, and at least a portion of the driving link has an edge radially protruding around the first rotary shaft.

The horizontal movement module further includes: a fifth link which is rotatably connected to the sixth rotary shaft spaced apart from the first rotary shaft in parallel with the first rotary shaft and is rotatably connected to a seventh rotary shaft spaced apart from the second rotary shaft in parallel with the second rotary shaft. The fifth link and the first link are parallel with each other.

The horizontal movement module further includes a sixth link which is rotatably connected to an eighth rotary shaft spaced apart from the second rotary shaft in parallel with the second rotary shaft, and is rotatably connected to a ninth rotary shaft spaced apart from the fifth rotary shaft in parallel with the fifth rotary shaft, and the sixth link and the fourth link are parallel with each other.

In another aspect of the present invention, the present invention provides an arm rest apparatus including: a fixed part fixed to an external object; a horizontal movement module having two-degree-of-freedom movement with respect to the fixed part; and a damping part which provides a resistance according to the two-degree-of-freedom movement of the horizontal movement module so as to control damping according to a horizontal movement of the arm.

The damping part includes first to third damping parts which respectively adjust angular speeds of first and second rotary shafts and an arm rotary shaft equally so as to control damping according to the horizontal movement.

The arm rest apparatus further includes: an arm support module which rotates around the arm rotary shaft and rotates around an inclination adjustment shaft while being supported by the horizontal movement module so as to allow a horizontal movement and a vertical movement; and a fourth damping part which adjusts an angular speed of the inclination adjustment shaft so as to control damping according to the vertical movement, wherein damping forces of the first to third damping part and damping force of the fourth damping part are adjusted differently.

The horizontal movement module includes: a first driving frame having a first link which is rotatably connected to the first rotary shaft and is rotatably connected to a second rotary shaft parallel with the first rotary shaft; and a second driving frame having a driving link which is rotatably connected to the first rotary shaft, wherein the first damping part forms a resistance when the first and second driving frames rotate around the first rotary shaft.

In a further aspect of the present invention, the present invention provides an arm rest apparatus including: a fixed part fixed to an external object; a horizontal movement module having two-translational-degree-of-freedom movement with respect to the fixed part; and an arm support module which is supported by the horizontal movement module to be movable and compensates weight of a user's arm.

The arm support module includes: first and second arm supporters on which a user's arm is supported; a first support part rotatably connected to an arm rotary shaft formed at the rotational end part; a rotary link rotatably mounted to an inclination adjustment shaft formed at the first support part;

and a gravity compensation part for providing elastic restoring force which increases as the rotary link gets further from the ground.

The gravity compensation part includes: an elastic body of which the length is changed according to a change in angle of the rotary link and which is arranged in parallel with the longitudinal direction of the rotary link; and a wire of which one end is fixed to the other end of the elastic body and the other end is connected to the first support part above the inclination adjustment shaft.

The rotary link includes a guide pulley for guiding the wire so that tensile force transferred to the elastic body from the wire is parallel with the longitudinal direction of the rotary link.

The arm rest apparatus according to an embodiment of the present invention can support the user's arm movements of all poses on a work space so as to reduce the degree of fatigue according to the user's arm movements.

The arm rest apparatus according to an embodiment of the present invention allows the user to move the arm accurately since allowing horizontal movement to which fixing and damping are applied.

DETAILED DESCRIPTION OF THE INVENTION

Hereinafter, Reference will be now made in detail to the preferred embodiments of the present disclosure with reference to the attached illustrative drawings. It should be noted that, in adding reference signs to the constituent elements in each of the drawings, the same constituent elements have the same reference signs even though they are illustrated in different figures. In addition, in the description of the present disclosure, when it is judged that detailed descriptions of known functions or structures may make the essential points vague, the detailed descriptions of the known functions or structures will be omitted.

Further, in the description of the constituent elements of the embodiments of the present disclosure, it is possible to use terms such as first, second, A, B, (a), (b) and the like. These terms are just to distinguish the constituent elements from any other constituent elements but do not limit the nature or sequence or order and the like of corresponding features by the terms. Additionally, it should be also understood that the expression that some constituent element is "connected", "coupled" or "joined" to another constituent element means that some constituent element may be directly connected or joined to another constituent element or is also "connected", "coupled" or "joined" to another constituent element through a further component therebetween.

A constituent element having the same function as another constituent element included in an embodiment is described as the same name in another embodiment. Unless explicitly described otherwise, description of any one embodiment can be applied to another embodiment, and a detailed description which is repeated will be omitted.

Figure 1:
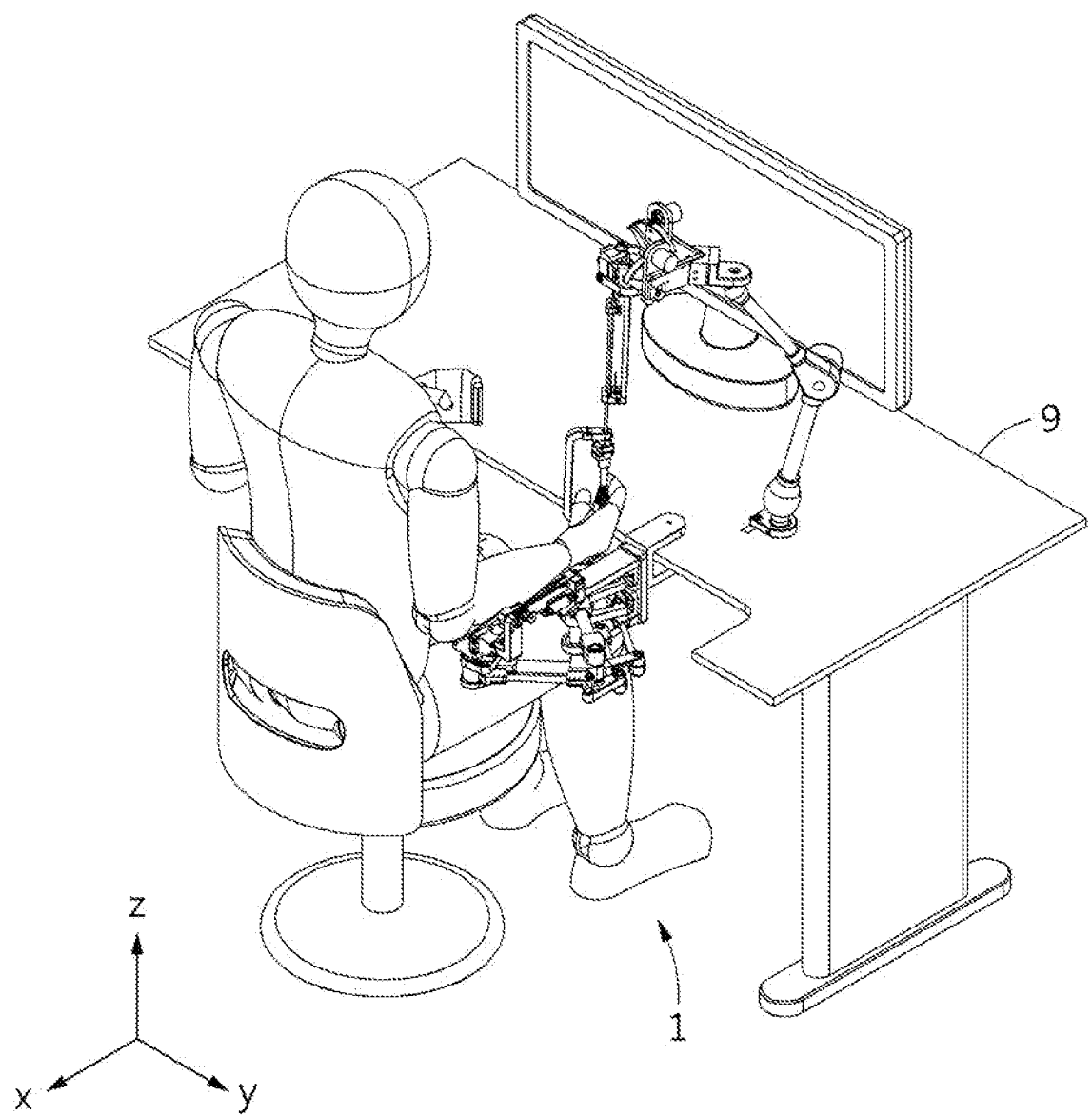
FIG. 1 is a perspective view illustrating the usage of an arm rest apparatus according to an embodiment of the present invention.
Figure 2:
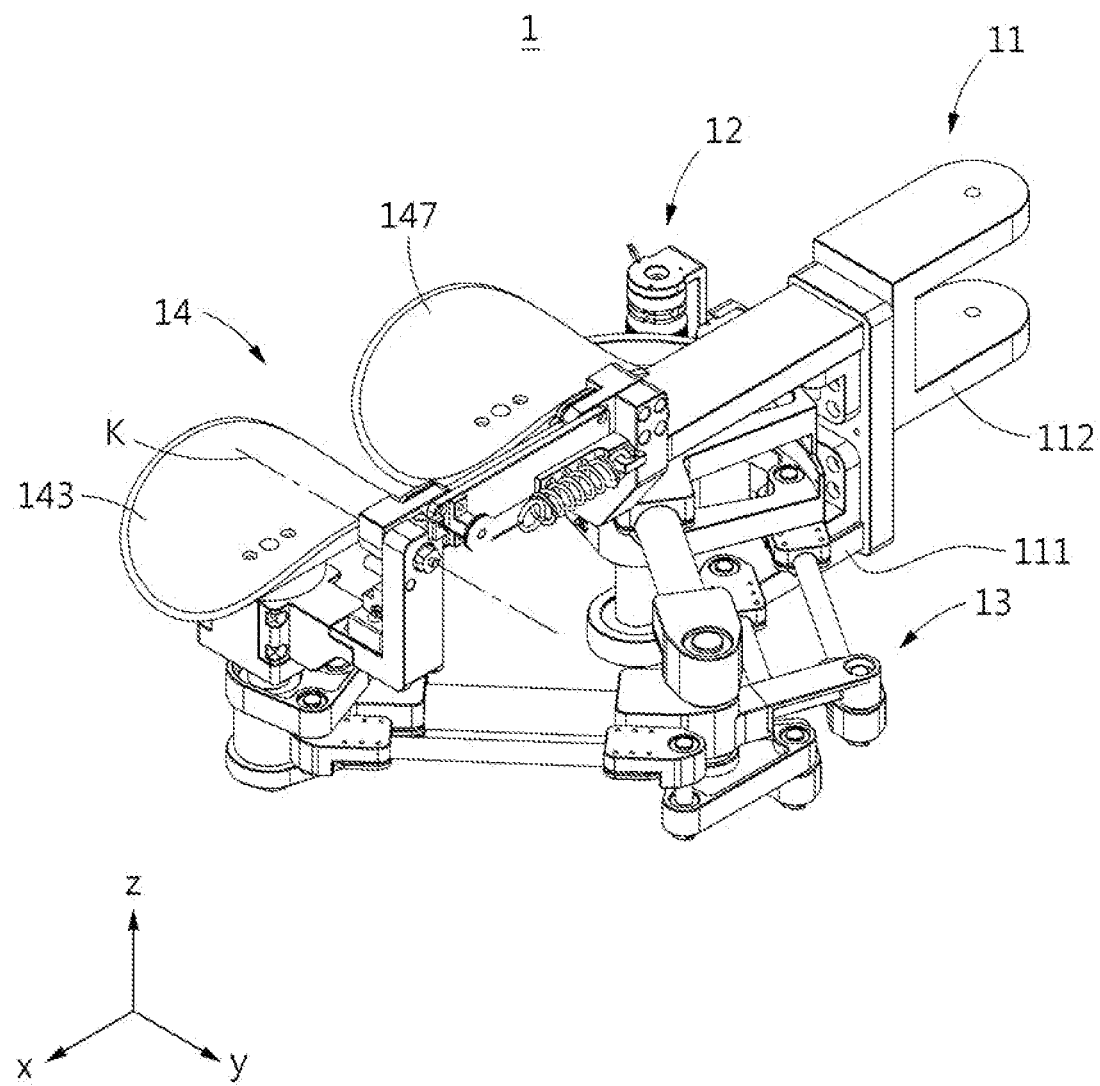
FIG. 2 is a perspective view of the arm rest apparatus according to the embodiment of the present invention.

FIG. 1 is a perspective view illustrating the usage of an arm rest apparatus according to an embodiment of the present invention, and FIG. 2 is a perspective view of the arm rest apparatus according to the embodiment of the present invention.

Referring to FIGS. 1 and 2, the arm rest apparatus 1 according to the embodiment of the present invention can support movement of a user's arm on a work space.

For instance, as illustrated in FIG. 1, the arm rest apparatus 1 is fixed on an external object 9 like a desk in order to support the user's arm movements in all poses on the work space. The arm rest apparatus 1 can relieve the degree of fatigue according to the user's arm movements and promote a horizontal movement to which fixing and damping are applied, so that the user can move the arm accurately.

The arm rest apparatus 1 according to the embodiment of the present invention includes a fixed part 11, a horizontal movement module 13, a damping part 12, and an arm support module 14.

The fixed part 11 is fixed on an external object 9 to provide a driving standard location of the arm rest apparatus 1.

For instance, the fixed part 11 includes: a fixing base 112 capable of being fixed to an external object; and a support base 111 connected to the fixing base 112 to support the horizontal movement module 13 and the arm support module 14 to be able to drive.

As illustrated in FIG. 1, the fixing base 112 can be fixed onto the external object 9, such as a desk, a shelf, and a table.

The support base 111 is fixed from the fixing base 112 to provide a relative rotation or a movement standard point of the horizontal movement module 13.

The horizontal movement module 13 can show the two-degree-of-freedom movement in the horizontal direction with respect to the fixed part 11. For instance, an end of the horizontal movement module 13 is rotatably connected around the support base 111, and the other end of the horizontal movement module 13 moves in the horizontal direction of the fixed part 11 and rotatably supports the arm support module 14.

The damping part 12 is connected to the horizontal movement module 13 so as to form resistance against the movement of the horizontal movement module 13. For instance, the resistance formed by the damping part 12 is controllable, so that the horizontal movement module 13 does not move completely and can change the movement speed even though the user applies uniform power.

The arm support module 14 is movably supported by the horizontal movement module 13 to support the user's arm. For instance, the arm support module 14 includes two arm supporters 143 and 147 which are reciprocally rotatable around rotary shafts respectively parallel with the horizontal direction where the horizontal movement module 13 moves.

In the description and drawings of the present invention, the horizontal direction based on the fixed part 11 is a direction on the plane parallel with the ground (the x-axis and y-axis in the drawing), and the vertical direction is a direction vertical to the ground (the z-axis in the drawing), but the horizontal direction and the vertical direction may be different from the coordinate axis of the ground according to the fixed position of the fixed part 11.

Referring to FIGS. 3 to 8, the horizontal movement module 13, the damping part 12, and the arm support module 14 will be described in detail.

Figure 3:
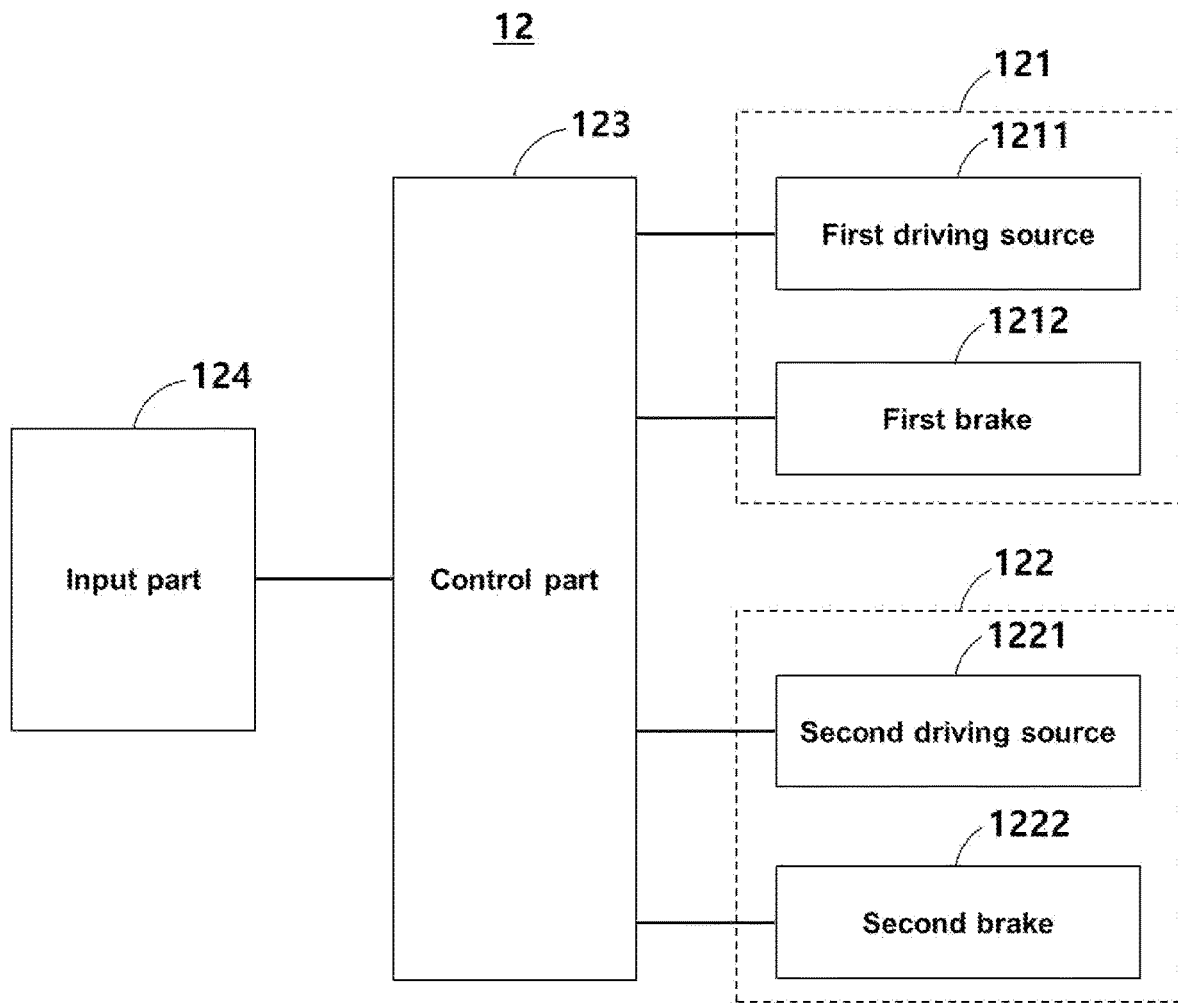
FIG. 3 is a block diagram of the arm rest apparatus according to the embodiment of the present invention.
Figure 4:
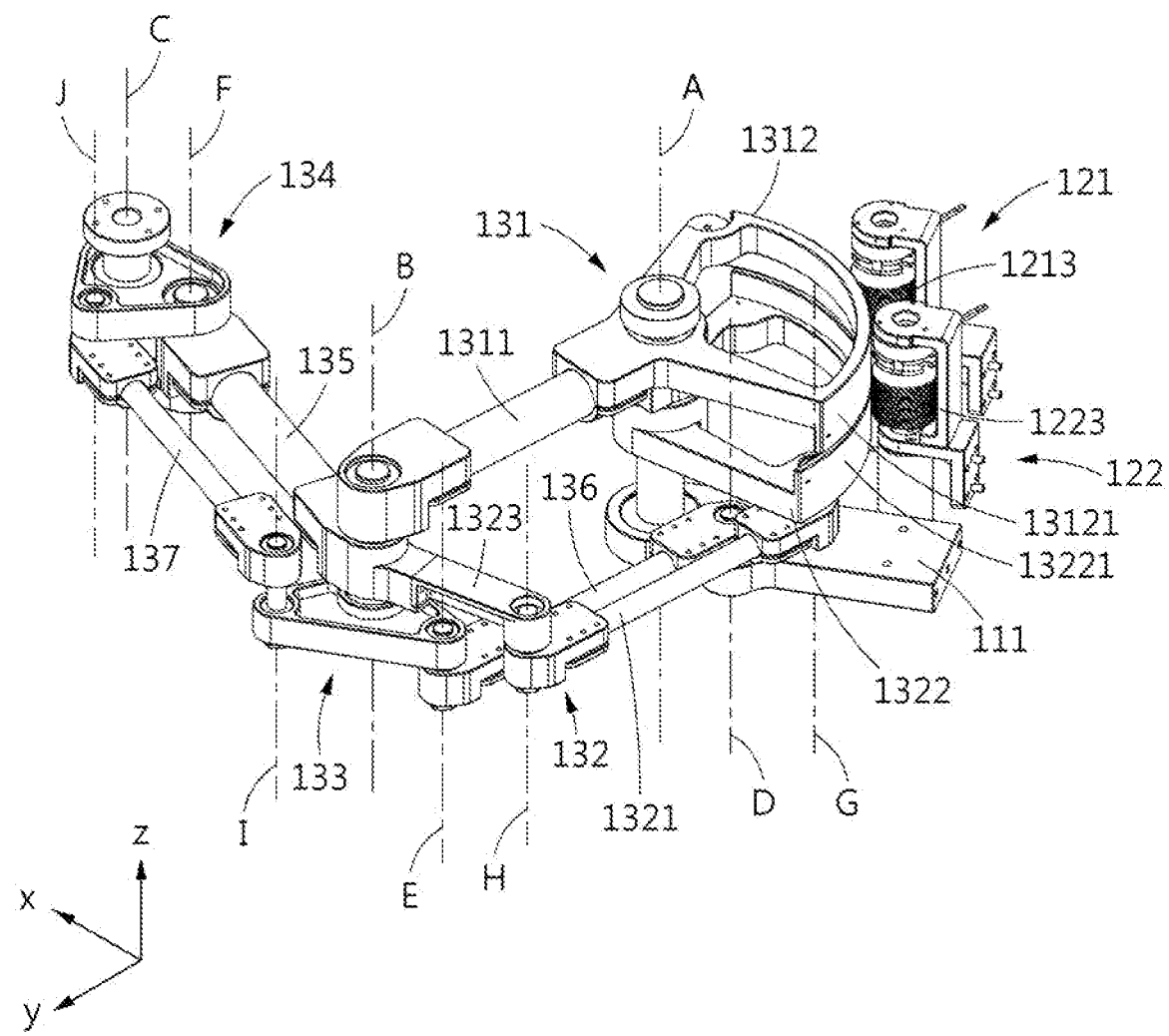
FIG. 4 is a perspective view of a horizontal movement module according to the embodiment of the present invention.
Figure 5:
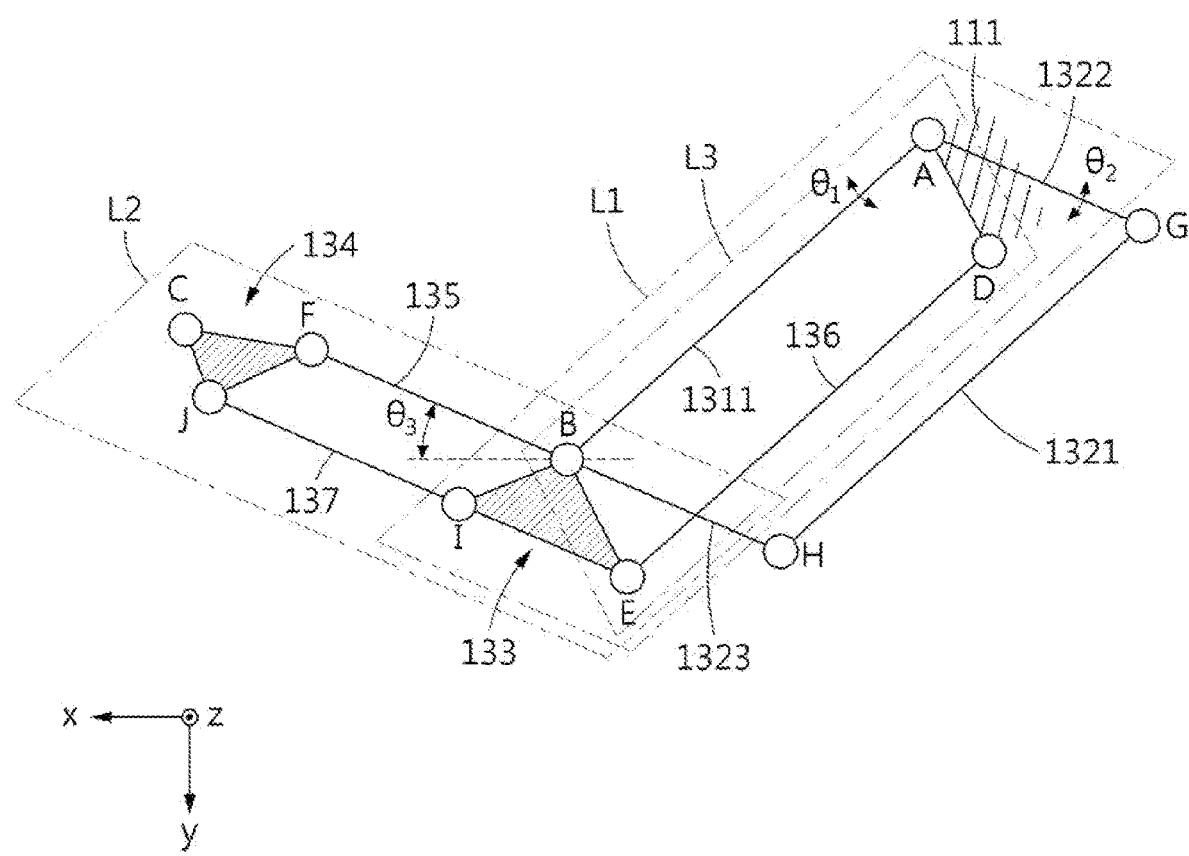
FIG. 5 is a plan view briefly illustrating an operational structure of the horizontal movement module according to the embodiment of the present invention.

FIG. 3 is a block diagram of the arm rest apparatus according to the embodiment of the present invention, FIG. 4 is a perspective view of a horizontal movement module according to the embodiment of the present invention, and FIG. 5 is a plan view briefly illustrating an operational structure of the horizontal movement module according to the embodiment of the present invention.

Referring to FIGS. 3 to 5, the structures of the horizontal movement module 13 and the damping part 12 according to the embodiment of the present invention will be described in detail.

The horizontal movement module 13 according to the embodiment of the present invention includes a first driving frame 131, a second driving frame 132, a central connection part 133, a rotational end part 134, and a plurality of links 135, 136 and 137.

The first driving frame 131 can rotate around a first rotary shaft (A) on the fixed part 11. For instance, an end of the first driving frame 13 can be connected onto the support base 111 to be rotatable around the first rotary shaft (A), and the other end of the first driving frame 13 can be connected onto the central connection part 133 to be rotatable around a second rotary shaft (B) parallel with the first rotary shaft (A).

For instance, the first driving frame 131 includes a first link 1311 connected between the first rotary shaft (A) and the second rotary shaft (B), and a first protrusion member 1312 fixed from the first link 1311 to rotate around the first rotary shaft (A).

At least a portion of the first protrusion member 1312 may have an arc-shaped edge protruding radially around the first rotary shaft (A) from the first link 1311. For instance, the first protrusion member 1312 is connected with a first damping part 121 which will be described later in order to form a resistance against the rotational motion of the first link 1311.

For instance, the first protrusion member 1312 includes a first contact surface 13121 which gets in contact with a first damping member 1213 of the first damping part 121 along the arc-shaped edge.

The second driving frame 132 may have a three joint link structure including three-point links 1322, 1321 and 1323 rotatably connected between the first rotary shaft (A) of the fixed part 11 and the second rotary shaft (B) of the central connection part 133.

The second driving frame 132 includes: a driving link 1322 connected to the fixed part to be rotatable around the first rotary shaft (A); a second link 1321 connected to the driving link 1322 to be rotatable around a third rotary shaft (G) parallel with the first rotary shaft (A); and a third link 1323 of which an end is connected to the second link 1321 to be rotatable around a fourth rotary shaft (H) spaced apart from the third rotary shaft (G) in parallel and of which the other end is connected to the central connection part 133 to be rotatable around the second rotary shaft (B).

The driving link 1322 is rotatably connected to the first rotary shaft (A) so that at least a portion has an arc-shaped edge protruding radially. For instance, the driving link 1322 may be called a second protrusion member 1322.

For instance, the second protrusion member 1322 includes a second contact surface 13221 which gets in contact with the second damping member 1223 of the second damping part 122 along the arc-shaped edge.

The first driving frame 131 and the second driving frame 132 may have a four-joint link structure, and the second link 1321 has the same length as a first link 1311 and the driving link 1322 has the same length as the third link 1323.

According to the above-mentioned structure, the links 1311, 1321, 1322 and 1323 may form a parallelogram to keep the facing links in parallel. Such a parallelogram structure can secure uniform stiffness even though a relatively light material is used, since having stiffness higher than other power transmission structures. For instance, some of the links 1311, 1321, 1322 and 1323 can be manufactured as a carbon fiber pipe which is five to ten times superior in stiffness to aluminum or steel pipe. So, the links can provide a lighter and stronger structure.

The central connection part 133 is connected from the first driving frame 131 and the second driving frame 132 and can move from the fixed part 11 in the horizontal direction to the fixed part 11.

The rotational end part 134 can be connected to the central connection part 133 through a plurality of the links 135 and 137 to be rotatable and movable, and includes an arm rotary shaft (C) on which the arm support module 14 will be mounted to be rotatable. For instance, the arm rotary shaft (C) is parallel with the first rotary shaft (A). The damping part for forming resistance against relative rotational motion between the members connected onto the arm rotary shaft (C) is mounted on the arm rotary shaft (C). The damping part provides a damping function to the movement of the arm rest apparatus 1 on the plane.

A plurality of the links 135, 136 and 137 are a fourth link 135, a fifth link 136, and a sixth link 137.

The fourth link 135 has an end which is connected to the central connection part 133 to be rotatable around the second rotary shaft (B) and the other end which is connected to the rotational end part 134 to be rotatable around the fifth rotary shaft (F) parallel with the first rotary shaft (A).

For instance, the fourth link 135 can be fixed to the third link 1323. So, when the third link 1323 rotates around the second rotary shaft (B), the fourth link 135 can rotate at the same time. In other words, the fourth link 135 and the third link 1323 can do a rigid body motion. From such a standpoint, it can be understood that the fourth link 135 and the third link 1323 may respectively designate different parts of one link.

The fifth link 136 has an end which is connected to the fixed part 11 to be rotatable around the sixth rotary shaft (D) spaced apart from the first rotary shaft (A) and being parallel with the first rotary shaft (A) and the other end which is connected to the central connection part 133 to be rotatable around a seventh rotary shaft (E) spaced apart from the second rotary shaft (B) and being parallel with the second rotary shaft (B).

Moreover, the fifth link 136 has the same length as the first link 1311. That is, the distance and direction that the sixth rotary shaft (D) is spaced apart from the first rotary shaft (A) on the fixed part 11 are equal to the distance and direction that the seventh rotary shaft (E) is spaced apart from the second rotary shaft (B) on the central connection part 133.

According to the above-mentioned structure, the first link 1311 and the fifth link 136 can always keep a parallel state so that the first link 1311 and the fifth link 136 between the fixed part 11 and the central connection part 133 provides a parallelogram joint structure to connect the first rotary shaft (A), the second rotary shaft (B), the seventh rotary shaft (E), and the sixth rotary shaft (D). At least one of the links 1311 and 136 which form the parallelogram can be manufactured as a carbon fiber pipe.

The sixth link 137 has an end which is connected to the central connection part 133 to be rotatable around an eighth rotary shaft (I) spaced apart from the second rotary shaft (B) in parallel with the second rotary shaft (B), and the other end which is connected to the rotational end part 134 to be rotatable around a ninth rotary shaft (J) spaced apart from the fifth rotary shaft (F) in parallel with the fifth rotary shaft (F).

Furthermore, the sixth link 137 has the same length as the fourth link 135. That is, the distance and direction that the eighth rotary shaft (I) is spaced apart from the second rotary shaft (B) on the central connection part 133 are equal to the distance and direction that the ninth rotary shaft (J) is spaced apart from the fifth rotary shaft (F) on the rotational end part 134.

According to the above-mentioned structure, the fourth link 135 and the sixth link 137 can always keep a parallel state so that the fourth link 135 and the sixth link 137 between the central connection part 133 and the rotational end part 134 provides a parallelogram joint structure to connect the second rotary shaft (B), the fifth rotary shaft (F), the eighth rotary shaft (I), and the ninth rotary shaft (J). At least one of the links 135 and 137 which form the parallelogram can be manufactured as a carbon fiber pipe.

Additionally, the arm rotary shaft (C) on the rotational end part 134 is formed at a point that is spaced apart from the fifth rotary shaft (F) and the ninth rotary shaft (J) in parallel, and the arm support module 14 is mounted to be rotatable around the arm rotary shaft (C) on the rotational end part 134.

Meanwhile, the support base 111, the central connection part 133, and the rotational end part 134 may be also called as "links". For instance, the support base 111 may be called a "fixed link" in that it is not moved relatively against the external object 9. As described above, through the connection structure of the three parallelograms 111-1311-133-136, 1311-1322-1321-1323, and 133-135-134-137 formed by a plurality of the links, the rotational end part 134 on which the arm support module 14 is mounted can show the two-degree-of-freedom movement in the horizontal direction with respect to the fixed part 11.

Hereinafter, referring to the conceptual diagram of FIG. 5, the link structure will be described in detail. The arm rest apparatus 1 includes (i) a first four-bar link structure, (ii) a second four-bar link structure which shares any one link with the first four-bar link, and (iii) a third four-bar link structure which shares another link with the first four-bar link and has a link fixed to any one link of the second four-bar link structure.

Here, any one among four links of the first four-bar link structure is the support base 111 which is fixed to the external object 9 to serve as a standard frame.

In detail, the first four-bar link structure includes the support base 111, the central connection part 133 spaced apart from the support base 111, and a pair of the links 1311 and 136 for connecting the support base 111 and the central connection part 133 with each other. According to the above-mentioned structure, the central connection part 133 shows the one-degree-of-freedom movement with respect to the support base 111. For instance, each of the links 1311 and 136 is longer than the maximum distance between the links 1311 and 136. Therefore, a movement radius of the central connection part 133 with respect to the support base 111 can be secured sufficiently.

The one link of the first four-bar link structure, which is shared with the second four-bar link structure, may be the central connection part 133 which is not directly connected to the support base 111.

In detail, the second four-bar link structure includes the central connection part, the rotational end part 134 spaced apart from the central connection part 133, and a pair of the links 135 and 137 for connecting the central connection part 133 and the rotational end part 134 with each other. According to the above-mentioned structure, the rotational end part 134 shows one-degree-of-freedom movement with respect to the central connection part 133, and finally, the rotational end part 134 shows two-degree-of-freedom movement with respect to the support base 111. Moreover, each of the links 135 and 137 is longer than the maximum distance between the links 135 and 137. Therefore, a work space of the rotational end part 134 with respect to the support base 111 can be secured sufficiently.

In general, such a four-bar link structure is greater in stiffness than the linear mechanism, but is narrower in work space than the linear mechanism. However, the arm rest apparatus 1 using the two four-bar link structures that share one link with each other like the present invention can overcome the problem of the conventional four-bar link structure, and provide high stiffness in a wide work space.

One link of the first four-bar link structure which is shared with the third four-bar link structure may be any one link 1311 among a pair of the links 1311 and 136 which is directly connected to the support base 111. Furthermore, one link of the second four-bar link structure which is fixed to any one link of the third four-bar link structure to be moved integrally with the link of the third four-bar link structure may be any one link 135 among a pair of the links 135 and 137 directly connected to the central connection part 133.

In detail, the third four-bar link structure includes the first link 1311, the second link 1321 spaced apart from the first link 1311, and a pair of the links 1322 and 1323 for connecting the first link 1311 and the second link 1321 with each other. Here, any one link 1323 among the links 1322 and 1323 is fixed to any one link 135 among the links 135 and 137 of the second four-bar link structure to be moved integrally with the link of the second four-bar link structure. According to the above-mentioned structure, because stiffness ranging to the rotational end part 134 with respect to the support base 111 can be reinforced, the present invention can provide a more stable structure. Additionally, as described later, because the damping part for forming resistance against the movement of the second four-bar link structure can be arranged at a position adjacent to the fixed part 11, for instance, a specific position on the fixed part 11 or a specific position on the external object 9, it can prevent that the inertia moment of the arm rest apparatus 1 is increased.

For instance, each of the three four-bar link structures has the parallelogram structure. Such a design can prevent generation of singularity during movement of the four-bar link structure so as to reduce the problem that the work space of the rotational end part 134 is limited. Meanwhile, the present invention is not limited to the above, and some or all of the three four-bar link structures may not be the parallelogram structure.

As described above, the arm rest apparatus 1 according to the present invention can enhance durability and movement stability since having the structure that can effectively disperse the user's arm weight and a vertical load of the arm support module 14 since a plurality of the links guide and support mutual movement and rotation.

Moreover, in order to reduce weight of the horizontal movement module 13 and inertia by movement, a plurality of the links may be empty hollow members.

The damping part 12 includes the first damping part 121, the second damping part 122, a control part 123, and an input part 124. At least a portion of the damping part 12 is mounted at a portion of the arm rest apparatus 1 that there is no movement, namely, at the fixed part 11, so as to prevent that the inertia moment of the arm rest apparatus 1 is increased. In another example, at least a portion of the damping part 12 may be mounted on the external object 9.

The first damping part 121 may form resistance against the rotational motion of the first driving frame 131.

Furthermore, the first damping part 121 includes: a first damping member 1213 connected to the first protrusion member 1312 to transfer a resistance according to a rotational motion of the first driving frame 131; a first driving source 1211 connected to the first damping member 1213 to form a resistance and to adjust intensity of the resistance; and a first brake 1212 which firmly fixes the first damping member 1213 to prevent rotation of the first driving frame 131.

The first damping member 1213 gets in contact with the first contact surface 13121, which is rounded, of the first protrusion member 1312. For instance, the connection between the first damping member 1213 and the first contact surface 13121 may be formed through various rotation transmission elements, such as gear coupling, screw coupling, friction material joining, and so on.

The first driving source 1211 can form a rotational resistance to the first damping member 1213 connected to the first contact surface 13121 and adjust intensity of the resistance. Additionally, the first driving source 1211 may be a driving source, such as a motor or a cylinder which can form rotary power with electric energy, pneumatic energy or hydraulic energy.

The first brake 1212 fixes the first damping member 1213, which is connected to the first contact surface 13121, not to rotate so that the first driving frame 131 is not rotated around the first rotary shaft (A). For instance, the first brake 1212 may be an electromagnetic brake which is operated by an electromagnetic method to press the first damping member 1213 powerfully.

The second damping part 122 can form a resistance against the rotational motion of the second driving frame 132.

Moreover, the second damping part 122 includes: a second damping member 1223 connected to the second protrusion member 1322 to transfer a resistance according to a rotational motion of the second driving frame 132; a second driving source 1221 connected to the second damping member 1223 to form a resistance and to adjust intensity of the resistance; and a second brake 1222 which firmly fixes the second damping member 1223 to prevent rotation of the second driving frame 132.

The second driving source 1221 can form a rotational resistance to the second damping member 1223 connected to the second contact surface 13221 and adjust intensity of the resistance. Additionally, the second driving source 1221 may be a driving source, such as a motor or a cylinder which can form rotary power with electric energy, pneumatic energy or hydraulic energy.

The second brake 1222 fixes the second damping member 1223, which is connected to the second contact surface 13221, not to rotate so that the second driving frame 132 is not rotated around the first rotary shaft (A). For instance, the second brake 1222 may be an electromagnetic brake which is operated by an electromagnetic method to press the second damping member 1223 powerfully.

Due to the structures of the first damping part 121 and the second damping part 122, the present invention can form a resistance according to the two-rotational-degree-of-freedom movement of the arm support module 14.

In detail, the first damping part 121 forms a resistance with respect to the movement with a first rotational degree of freedom (θ1) that the first driving frame 131 rotates around the first rotary shaft (A), so as to suppress the tendency that the central connection part 133 rotates with respect to the fixed part 11.

The second damping part 122 forms a resistance with respect to the movement with a second rotational degree of freedom (θ2) that the second driving frame 132, namely, the driving link 1322, rotates around the first rotary shaft (A), so as to suppress the tendency that the rotational end part 134 rotates with respect to the central connection part 133.

Finally, the damping part 12 forms damping power to resist against power applied to the rotational end part 134 according to changes in the user's arm movements and poses, so that the user can guide to move the arm accurately and slowly.

In addition, the user can adjust intensity of the resistance formed by the first damping part 121 or the second damping part 122 so as to provide appropriate damping control according to kinds of work, accuracy, or the user's taste.

Moreover, as occasion demands, the first brake 1212 or the second brake 1222 is operated to suppress rotation of the first driving frame 131 or the second driving frame 132 in order to prevent the horizontal movement of the rotational end part 134. Therefore, the user's arm supported by the arm support module 14 can be fixed in horizontal position or pose. So, the arm rest apparatus according to the present invention is effective in performing work requiring accurate movements utilizing tiny muscles below the wrist.

In the meantime, the first damping part 121 and the second damping part 122 are operated individually, namely, the movement with the first rotational degree of freedom (θ$_1$) and the movement with the second rotational degree of freedom (θ$_2$) are different in the degree of suppression. So, the arm rest apparatus 1 according to the present invention can selectively induce arm movements according to kinds of work or arm movement races.

The control part 123 operates the first damping part 121 or the second damping part 122 so that the first driving frame 131 or the second driving frame 132 can form a resistance against the rotational motion performed around the first rotary shaft (A), and adjusts intensity of the resistance.

The control part 123 operates the first brake 1212 or the second brake 1222 so that the first driving frame 131 or the second driving frame 132 can suppress the rotational motion performed around the first rotary shaft (A).

The input part 124 includes an interface which receives an input signal from the user in order to control the first damping part 121 or the second damping part 122.

However, it is not necessary that the first damping part 121 and the second damping part 122 respectively and individually form resistances against the rotational motions of the driving frames 131 and 132. As illustrated in FIG. 4, if the first protrusion member 1312 of the first driving frame 131 and the driving link 1322 of the second driving frame 132 rotate around the same rotary shaft (A), it is possible to simultaneously provide damping force to the first driving frame 131 and the second driving frame 132 using the one damping part. For instance, it would be understood that the first damping member 1213 getting in contact with the first protrusion member 1312 and the second damping member 1223 getting in contact with the second protrusion member 1322 are respectively parts of the same component.

Figure 6:
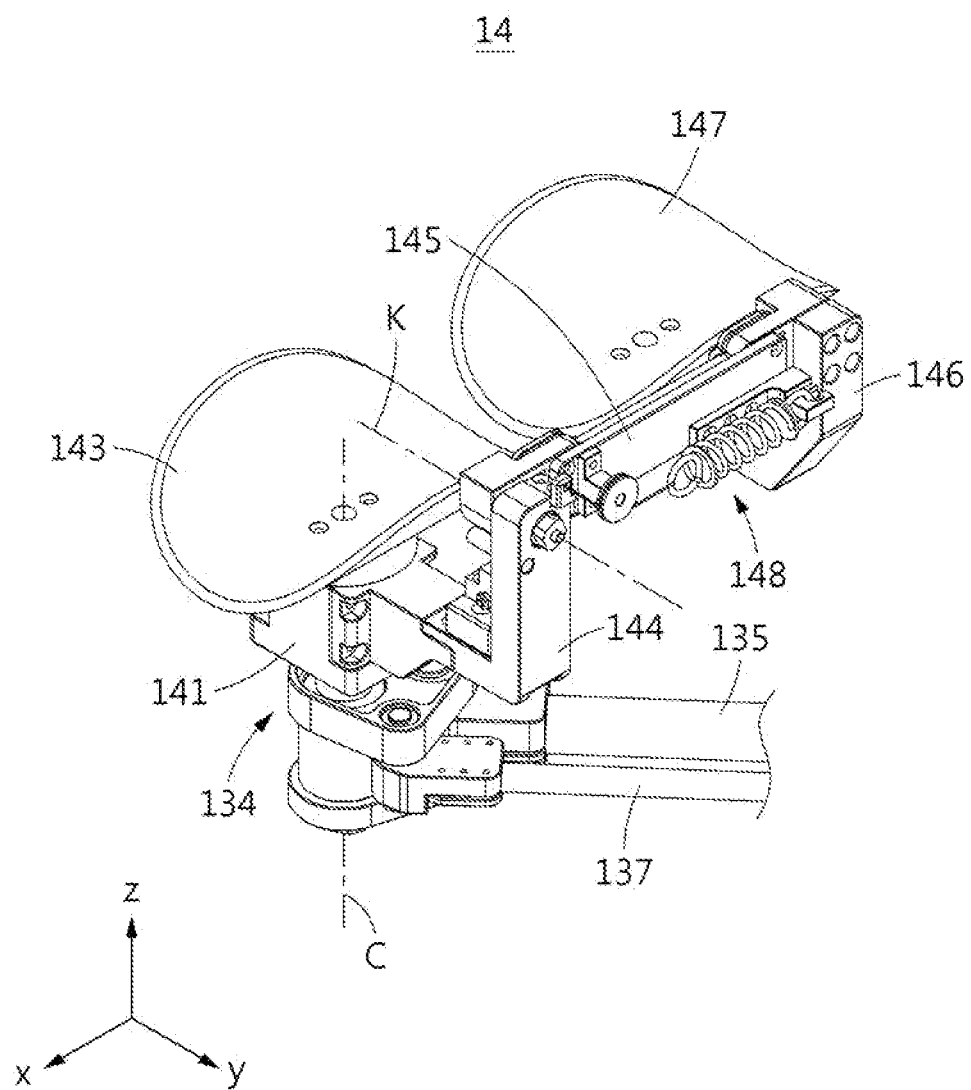
FIG. 6 is a perspective view of an arm support module according to the embodiment of the present invention.
Figure 7:
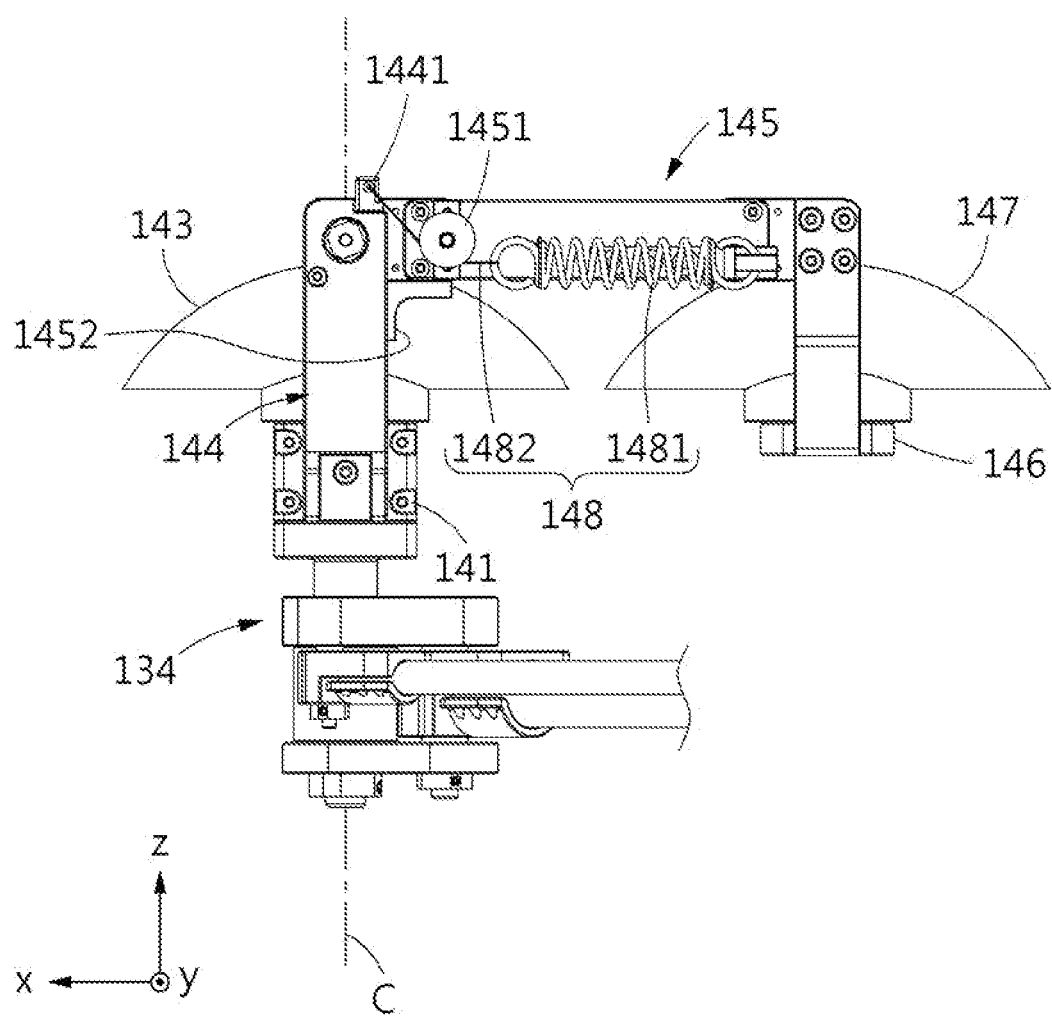
FIGS. 7 and 8 are side views of the arm support module according to the embodiment of the present invention.
Figure 8:
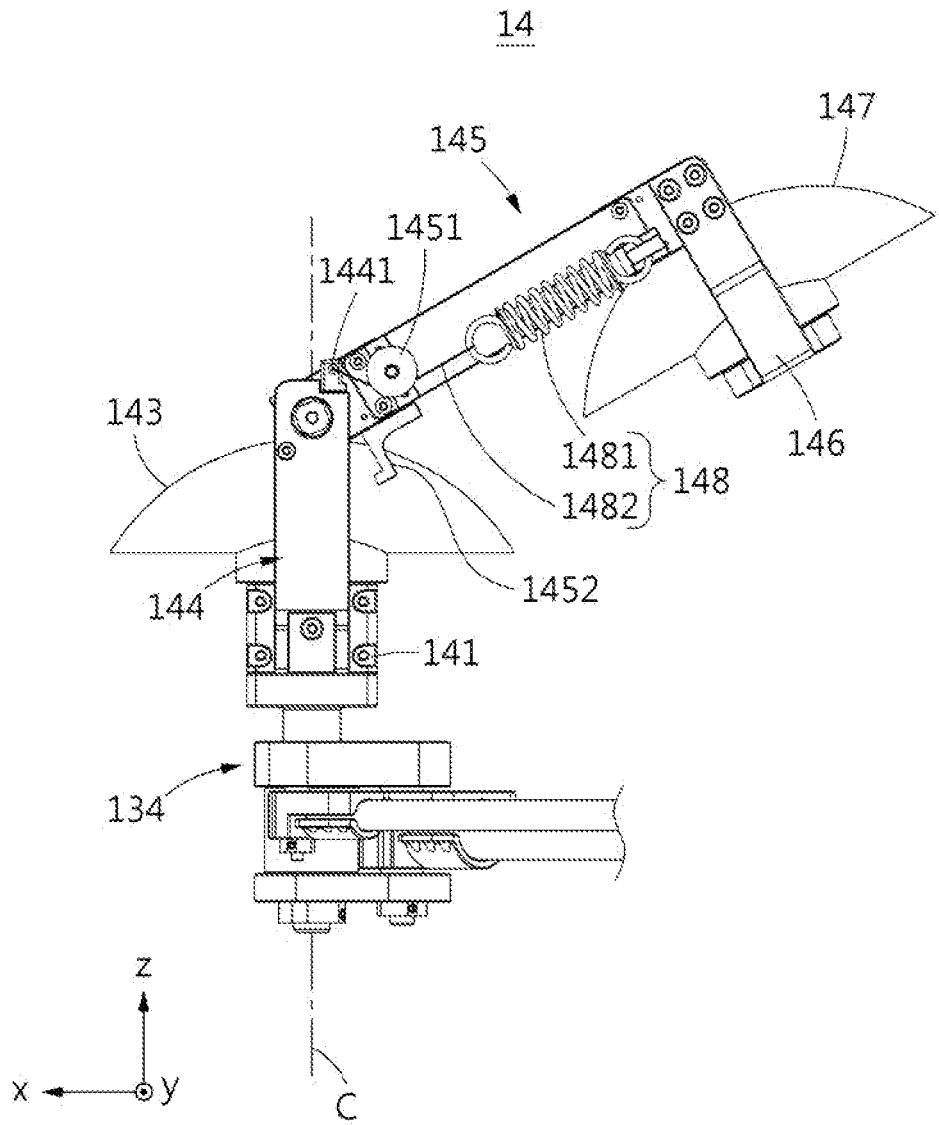

FIG. 6 is a perspective view of an arm support module according to the embodiment of the present invention, and FIGS. 7 and 8 are side views of the arm support module according to the embodiment of the present invention.

Referring to FIGS. 6 to 8, the arm support module 14 according to the embodiment of the present invention will be described in detail.

The arm support module 14 according to the embodiment of the present invention includes a connection part 141, a first support part 144, a first arm supporter 143, a rotary link 145, a second support part 146, a second arm supporter 147, and a weight compensation part 148.

The connection part 141 is mounted on the rotational end part 134 to be rotatable around the arm rotary shaft (C).

The first support part 144 is fixed to the connection part 141 to support the first arm supporter 143. Moreover, the first support part 144 is formed integrally with the connection part 141 to be rotated around the arm rotary shaft (C).

The first arm supporter 143 can support the user's arm. For instance, the first arm supporter 143 can support the user's arm, namely, a part near to the elbow.

Furthermore, the surface of the first arm supporter 143 has a shape of which both edge portions are curved upwards so that the user's arm is put on the first arm supporter stably to be supported.

As illustrated in FIGS. 7 and 8, the first arm supporter 143 is overlapped with the arm rotary shaft (C) in order to stably guide the rotational motion of the forearm part based on the elbow joint.

The rotary link 145 may be a link that one side is rotatably connected to the first support part 144 and the other side is connected to the second support part 146.

Additionally, the rotary link 145 can rotate around an inclination adjustment shaft (K) with respect to the first support part 144, and the inclination adjustment shaft (K) is vertical to the arm rotary shaft (C). The damping part which forms the resistance against the relative rotational motion of the members connected to the inclination adjustment shaft (K) is mounted on the inclination adjustment shaft (K). Such a damping part provides damping force to the movements of the arm rest apparatus 1.

The second support part 146 is connected to the rotary link 145 to support the second arm supporter 147.

The second arm supporter 147 can support the user's arm. For instance, the second arm supporter 147 can support the user's arm, namely, a part near to the elbow.

Furthermore, the surface of the second arm supporter 147 has a shape of which both edge portions are curved upwards so that the user's arm is put on the first arm supporter stably to be supported.

The weight compensation part 148 can compensate influences of the weight of the user's arm and the weight of the arm support module 14.

Moreover, the weight compensation part 148 includes an elastic body 1481 mounted on the rotary link 145, and a wire 1482 connected between the elastic body 1481 and the first support part 144.

The elastic body 1481 has an end fixed to the rotary link 145 and the other end connected to the wire 1482. As illustrated in FIGS. 6 to 8, the elastic body 1481 may be a spring mounted to be expandable in the longitudinal direction of the rotary link 145.

The wire 1482 applies tensile force to the elastic body 1481 between the elastic body 1481 and the first support part 144. Due to the structure of the wire 1482, intensity of the tensile force applied to the elastic body 1481 can be adjusted according to a rotational angle formed with respect to the inclination adjustment shaft (K).

That is, a part where the wire 1482 is connected to the first support part 144 is formed above a part where the inclination adjustment shaft is located at the first support part 144 in the vertical direction. Here, the part where the wire 1482 is fixed to the first support part 144 may be called a wire fixing part 1441.

Due to the above-mentioned structure, a distance between the wire fixing part 1441 and an end portion of the elastic body 1481 gets further as the rotary link 145 gets further from the ground in the vertical direction (z-axis direction).

In other words, when the rotary link 145 rotates from an upwardly inclined state as illustrated in FIG. 8 to a horizontal state, tensile force applied to the elastic body 1481 is increased, and at the same time, restoring force formed from the elastic body 1481 is also increased.

Finally, because the restoring force of the elastic body 1481 can form power to upwardly move the second arm supporter 147 relative to the first arm supporter 143, while the user's forearm pose is changed to be inclined upwards, influences of weight of the user's arm and weight of the arm support module 14 can be reduced or compensated.

Moreover, the rotary link 145 includes a guide pulley 1451 for guiding a connection direction of the wire 1482 between the first support part 144 and the elastic body 1481 in order to keep the direction of tensile force transferred to the elastic body 1481 from the wire 1482 in parallel with the direction of the rotary link 145.

As illustrated in FIGS. 7 and 8, due to the guide pulley 1451, because the wire 1482 extending from the wire fixing part 1441 can be connected to the elastic body 1481 in parallel with the extension direction of the rotary link 145 after being wound on a part of the guide pulley 1451, the tensile force applied to the elastic body 1481 can be adjusted approximately linearly according to the rotational angle of the rotary link 145.

Furthermore, the rotary link 145 includes an interference part 1452, which is interfered by the first support part 144, in order not to be rotated beyond a set angle with respect to the first support part 144.

Additionally, if the first arm supporter 143 and the second arm supporter 147 keep parallel with each other or if the rotary link 145 is rotated to direct a horizontal direction to the inclined adjustment shaft as illustrated in FIG. 7, the interference part 1452 is interfered by the first support part 144 so that the rotary link 145 is not rotated in a downwardly inclined direction from the inclined adjustment shaft.

The arm rest apparatus 1 according to the embodiment of the present invention can stably guide the two-degree-of-freedom movement in the horizontal direction in the state where the user's arm is supported, and at the same time, the arm support module 14 can stably compensate weight of the arm in various poses by applying a gravity compensation mechanism according to a vertical inclination of the arm.

Finally, the arm rest apparatus 1 according to the embodiment of the present invention can ergonomically support the user's arm in all poses and minimize the user's fatigue according to movements.

The arm rest apparatus 1 according to the embodiment of the present invention can show accurate and exact movement according to characteristics of work since the damping part 12 can control damping according to the horizontal movement of the arm.

In addition, if the arm rest apparatus 1 is used under a surgery situation, the user can increase damping force of the horizontal movement module 13 so as to accurately and slowly move an end of a surgical instrument grasped by the hand near a patient's lesion. Therefore, the arm rest apparatus 1 according to the present invention can filter unintended fast and big movement of the arm so as to prevent an unexpected injury formed on the patient's lesion.

The arm rest apparatus 1 according to the present invention is very effective for accurate work utilizing tiny muscles below the wrist since the brakes 1212 and 1222 can fix the horizontal position of the arm support module 14.

In another embodiment of the damping part, the damping part includes first to fourth damping parts. The first to third damping parts can respectively adjust angular speeds of the first and second rotary shafts (A and B) and the arm rotary shaft (C) equally by controlling damping according to the horizontal movement. Therefore, the damping forces of the first and second rotary shafts (A and B) and the arm rotary shaft (C) are reduced equally. Through the adjustment of the angular speeds of the first and second rotary shafts (A and B) and the arm rotary shaft (C) reduces a movement speed of the horizontal direction (x-axis and y-axis directions).

Moreover, the arm support module 14 rotates around the arm rotary shaft (C), and rotates around the inclination adjustment shaft (K) while being supported by the horizontal movement module 13, so as to make horizontal movement and vertical movement possible. That is, the arm support module 14 allows the horizontal movement in the horizontal direction (x-axis and y-axis direction), and allows the vertical movement in the vertical direction (z-axis direction) which causes a change in height of the arm. Therefore, the fourth damping part can control damping according to the vertical movement of the arm support module 14 so as to adjust the angular speed of the inclination adjustment shaft. A change speed in height of the arm supported by the arm support module 14 can be adjusted according to the damping force of the fourth damping part.

Meanwhile, the damping forces of the first to third damping parts and the damping force of the fourth damping part can be adjusted differently. That is, preferably, in case of a surgery requiring more accurate X-axis and Y-axis horizontal movement, the damping forces of the first to third damping parts must be greater than the damping force of the fourth damping part, but in case of a surgery requiring more accurate Z-axis vertical movement or depth movement, the damping force of the fourth damping part must be greater than the damping forces of the first to third damping parts.

Although the embodiments of the present invention have been described by the limited drawings, various modifications and variations are possible to those skilled in the art from the above description. For example, the described techniques may be performed in a different order than the described method, and/or components of the described systems, structures, devices, circuits, etc. may be combined or combined in a different form than the described method, or other components. Or even if replaced or substituted by equivalents, an appropriate result can be achieved.

What is claimed is:

1. An arm rest apparatus comprising:
    a fixed part fixed to an external object;
    a horizontal movement module having one end rotatably connected to the fixed part and another end having two-translational-degree-of-freedom movement with respect to the fixed part, wherein the horizontal movement module further comprises:
        a first driving frame which has a first link rotatably connected to a first rotary shaft and rotatably connected to a second rotary shaft parallel with the first rotary shaft, wherein the first driving frame further comprises a first protrusion member which is fixed to the first link to rotate around the first rotary shaft and has an edge radially protruding around the first rotary shaft;
        a second driving frame which has a driving link rotatably connected to the first rotary shaft, a second link rotatably connected to a third rotary shaft parallel with the first rotary shaft, and a third link rotatably connected to a fourth rotary shaft spaced apart from the third rotary shaft in parallel with the third rotary shaft and rotatably connected to the second rotary shaft, wherein at least a portion of the driving link has an edge radially protruding around the first rotary shaft;
        a central connection part which is rotatably connected to the fixed part through a plurality of links; and
        a rotational end part which is rotatably connected to the central connection part through a plurality of links; and
    an arm support module movably supported by the horizontal movement module.

2. The arm rest apparatus according to claim 1, wherein the horizontal movement module further comprises a fourth link which is rotatably connected to the second rotary shaft and is rotatably connected to a fifth rotary shaft parallel with the first rotary shaft, and
    wherein the fourth link is fixed to the third link so as to rotate around the second rotary shaft together.

3. The arm rest apparatus according to claim 2, wherein the horizontal movement module further comprises:
    a fifth link which is rotatably connected to a sixth rotary shaft spaced apart from the first rotary shaft in parallel with the first rotary shaft and is rotatably connected to a seventh rotary shaft spaced apart from the second rotary shaft in parallel with the second rotary shaft, and
    wherein the fifth link and the first link are parallel with each other.

4. The arm rest apparatus according to claim 3, wherein the horizontal movement module further comprises:
    a sixth link which is rotatably connected to an eighth rotary shaft spaced apart from the second rotary shaft in parallel with the second rotary shaft, and is rotatably connected to a ninth rotary shaft spaced apart from the fifth rotary shaft in parallel with the fifth rotary shaft, and
    wherein the sixth link and the fourth link are parallel with each other.

5. An arm rest apparatus comprising:
    a fixed part fixed to an external object;
    a horizontal movement module having two-degree-of-freedom movement with respect to the fixed part, wherein the horizontal movement module further comprises:
        a first driving frame which has a first link rotatably connected to a first rotary shaft and rotatably connected to a second rotary shaft parallel with the first rotary shaft;
        a second driving frame which has a driving link rotatably connected to the first rotary shaft, a second link rotatably connected to a third rotary shaft parallel with the first rotary shaft, and a third link rotatably connected to a fourth rotary shaft spaced apart from the third rotary shaft in parallel with the third rotary shaft and rotatably connected to the second rotary shaft;
        a central connection part which is rotatably connected to the fixed part through a plurality of links; and a rotational end part which is rotatably connected to the central connection part through a plurality of links; and a damping part which provides a resistance according to the two-degree-of-freedom movement of the horizontal movement module so as to control damping according to a horizontal movement of an arm, wherein the damping part comprises:

a first damping part, a second damping part, and a third damping part which respectively adjust angular speeds of first and second rotary shafts and an arm rotary shaft equally so as to control damping according to the horizontal movement.

6. The arm rest apparatus according to claim 5, wherein the first damping part forms a resistance when the first and second driving frames rotate around the first rotary shaft.

7. An arm rest apparatus comprising:

a fixed part fixed to an external object;

a horizontal movement module having two-translational-degree-of-freedom movement with respect to the fixed part; and an arm support module which is supported by the horizontal movement module to be movable and compensates weight of a user's arm, wherein the arm support module comprises:

a first arm supporter and a second arm supporter;

a first support part rotatably connected to an arm rotary shaft formed at a rotational end part;

a rotary link rotatably mounted to an inclination adjustment shaft formed at the first support part; and a gravity compensation part for providing elastic restoring force which increases as the rotary link gets further from a ground wherein the gravity compensation part comprises: an elastic body of which the length is changed according to a change in angle of the rotary link and which is arranged in parallel with the longitudinal direction of the rotary link; and a wire of which one end is fixed to an end of the elastic body and an other end of the wire is connected to the first support part above the inclination adjustment shaft.

8. The arm rest apparatus according to claim 7, wherein the rotary link comprises a guide pulley for guiding the wire so that tensile force transferred to the elastic body from the wire is parallel with the longitudinal direction of the rotary link.

\* \* \* \* \*